(12) United States Patent
Higeta et al.

(10) Patent No.: US 9,605,240 B2
(45) Date of Patent: Mar. 28, 2017

(54) FLUID DELIVERY SYSTEM

(71) Applicant: MEDINET CO., LTD., Yokohama-shi, Kanagawa (JP)

(72) Inventors: Daisuke Higeta, Yokohama (JP); Tetsuya Yagura, Yokohama (JP); Shun Ogasawara, Yokohama (JP); Kazumi Ota, Yokohama (JP); Takahiro Sato, Yokohama (JP); Nao Yoshinaga, Yokohama (JP); Hiroshi Terakawa, Yokohama (JP)

(73) Assignee: MEDINET CO., LTD. (JP)

( * ) Notice: Subject to any disclaimer, the term of this patent is extended or adjusted under 35 U.S.C. 154(b) by 0 days.

(21) Appl. No.: 14/915,681

(22) PCT Filed: Sep. 2, 2014

(86) PCT No.: PCT/JP2014/073098
§ 371 (c)(1),
(2) Date: Mar. 1, 2016

(87) PCT Pub. No.: WO2015/033940
PCT Pub. Date: Mar. 12, 2015

(65) Prior Publication Data
US 2016/0194592 A1    Jul. 7, 2016

(30) Foreign Application Priority Data

Sep. 3, 2013  (JP) .................................. 2013-182498

(51) Int. Cl.
*B01L 3/00*          (2006.01)
*C12M 1/00*          (2006.01)
(Continued)

(52) U.S. Cl.
CPC ............ *C12M 29/04* (2013.01); *C12M 23/26* (2013.01); *C12M 41/00* (2013.01); *F04B 43/1269* (2013.01)

(58) Field of Classification Search
CPC ........................................................ B01L 3/02
See application file for complete search history.

(56) References Cited

U.S. PATENT DOCUMENTS

| 2,696,173 | A |   | 12/1954 | Jensen |             |
|-----------|---|---|---------|--------|-------------|
| 3,787,148 | A | * | 1/1974  | Kopf   | F04B 43/1276 |
|           |   |   |         |        | 417/477.8   |

(Continued)

FOREIGN PATENT DOCUMENTS

| JP | S47038485 B1 | 9/1972 |
| JP | S60189834 U  | 12/1985 |

(Continued)

OTHER PUBLICATIONS

Extended European Search Report for EP Application No. 14842077.1, dated Jun. 9, 2016 (7 pages).

*Primary Examiner* — Jyoti Nagpaul
(74) *Attorney, Agent, or Firm* — Harness, Dickey & Pierce, P.L.C.

(57) ABSTRACT

To avoid contamination of workspaces by splashing and the like of a waste fluid. A fluid delivery system for delivering a fluid from one container to another container includes: a delivery channel connecting between the one container to the other container; and a delivery pump which feeds the fluid into the delivery channel by compressively deforming inner diameter in the middle of the delivery channel, wherein the delivery channel is a partially elastic configuration that can be compressively deformed by the delivery pump, and also is a closed-system configuration with which the fluid flowing inside thereof is isolated from outside. As described, the delivery pump and the delivery tube or the (Continued)

waste-fluid container are not directly connected but are simply in contact. Therefore, it is possible to prevent splashing and the like of the waste fluid onto a work space when handling the waste fluid.

10 Claims, 14 Drawing Sheets

(51) Int. Cl.
  *F04B 43/12* (2006.01)
  *C12M 1/34* (2006.01)

(56) References Cited

U.S. PATENT DOCUMENTS

| | | | |
|---|---|---|---|
| 4,196,743 A | 4/1980 | Kampf et al. | |
| 4,832,685 A * | 5/1989 | Haines | A61F 9/00745 604/30 |
| 7,478,999 B2 | 1/2009 | Limoges | |
| 2002/0039544 A1* | 4/2002 | Schroeder | B01L 3/02 422/400 |
| 2011/0094619 A1 | 4/2011 | Steel et al. | |
| 2012/0034105 A1 | 2/2012 | Hillman | |

FOREIGN PATENT DOCUMENTS

| | | |
|---|---|---|
| JP | H05238 A | 1/1993 |
| JP | 2007105654 A | 4/2007 |
| JP | 2007526424 A | 9/2007 |
| JP | 2011006466 A | 1/2011 |
| JP | 2011525142 A | 9/2011 |
| WO | WO-2004-088136 A2 | 10/2004 |

* cited by examiner

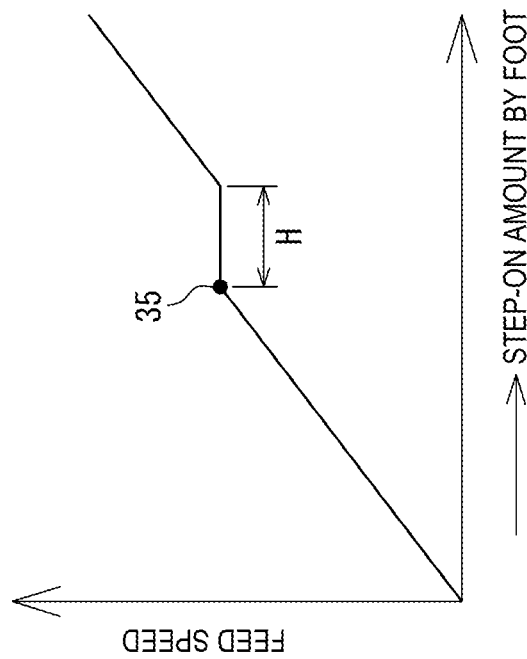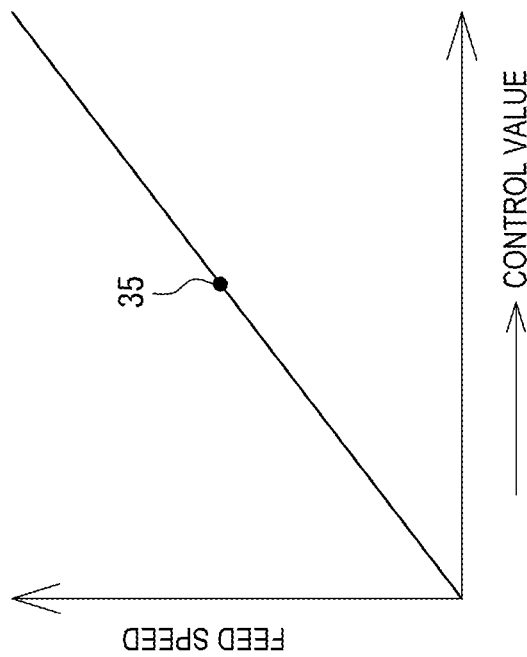

FLUID DELIVERY SYSTEM

CROSS-REFERENCE TO RELATED APPLICATIONS

This application is a U.S. National Phase application under 35 U.S.C. 371 of International Application No. PCT/JP2014/073098, filed Sep. 2, 2014 and published in Japanese as WO 2015/033940 A1 on Mar. 12, 2015. This application claims priority to Japanese Patent Application 2013-182498, filed on Sep. 3, 2013. The entire disclosures of the above applications are incorporated herein by reference.

TECHNICAL FIELD

The present invention relates to a fluid delivery system for delivering a fluid from one container to another container and, more specifically, to a fluid delivery system for delivering a culture fluid or the like used in cell culture to another container.

BACKGROUND ART

Various kinds of configurations have been developed as the fluid delivery systems for delivering a fluid from one container to another container, and those kinds of fluid delivery systems are used when delivering various kinds of fluids in studies of chemistry and biology, product manufacture, medical services, and the like, for example (JP-A No. 2011-6466, JP-T No. 2007-526424).

In the work of cell culture, cultured cells and a fluid such as a used medium and the like (referred to as a waste fluid hereinafter) are separated by means of settling, centrifugation, or the like, and the waste fluid is aspirated by a pump and delivered to a waste fluid storage container.

Conventionally, a vacuum pump is used for the work of aspirating the waste fluid. With the vacuum pump, the delivered waste fluid is stored in a waste fluid storage container such as a waste fluid bottle or the like. When a specific amount is stored or a series of work is completed, the waste fluid storage container such as the waste fluid bottle and a fluid delivering part such as a fluid delivery tube connecting to the waste fluid storage container from a aspiration part need to be detached and also the waste fluid stored in the waste fluid storage container needs to be transferred to a disposable container through decantation or the like. In that case, the waste fluid may be splashed and may contaminate the workspace.

Also, when aspirating the waste fluid, it is required to discard the waste fluid without influencing the cultured cells. For satisfying such demand, in a case where the amount of the waste fluid is great within one container, there is no influence imposed upon the cultured cells even when the waste fluid is aspirated abruptly since the aspiration port of the delivery pump is distant from the cultured cells. However, when the waste fluid is disposed and the remaining amount of the waste fluid becomes small, the aspiration port of the delivery pump becomes closer to the cultured cells. Therefore, it is necessary to slow the aspiration speed of the delivery pump.

As described, in order to control the aspiration speed of the delivery pump, it is necessary to control the feed speed of the delivery pump. In order to control the feed speed of the delivery pump, it is common to output control values for controlling the feed speed linearly.

SUMMARY OF INVENTION

Technical Problem

However, when the control values for controlling the feed speed is outputted linearly from the controller to the delivery pump, the feed speed of the delivery pump corresponds to the control values from the controller on one-on-one basis. Therefore, a radical change occurs in the aspiration speed on the aspiration port side of the delivery pump under a state where the waste fluid is disposed and the remaining amount of the waste fluid is reduced so that the aspiration port comes to be close to the cultured cells. Thus, the waste fluid may be ruffled and the cultured cells may be stirred or the cells may also be aspirated mistakenly, thereby influencing the cultured cells.

In order to overcome such situation, it is necessary to control the speed for not generating ruffling of the waste fluid when controlling the feed speed of the delivery pump by the controller, which complicates the configuration for controlling the speed.

An object of the present invention is to provide a fluid delivery system for avoiding contamination of the workspace caused by splashing and the like of the waste fluid.

Another object of the present invention is to provide a fluid delivery system capable of suppressing stirring and re-mixture of a waste fluid separated in a container, for example, with cultured cells through adjusting the feed speed of the fluid according to the remaining amount of the fluid in the container.

Solution to Problem

The workspace for conducting culture of cells, particularly the spaces for culturing cells used for regeneration/cellular therapy, are required to have no contamination of the waste fluid. When handling samples containing an infectious substance, there is a possibility of having contamination by splashing of the solution containing the infectious substance. Therefore, it is extremely important to prevent diffusion to the public health and eliminate a risk of infecting the operators. For that, it is required to use a closed fluid delivery system. However, there has been no system built to be properly used for handling waste fluids.

Thereby, the fluid delivery system according to the present invention is a fluid delivery system for delivering a fluid from one container to another container, which includes: a delivery channel connecting between the one container to the other container; and a delivery pump which feeds the fluid into the delivery channel by compressively deforming inner diameter in middle of the delivery channel, characterized in that the delivery channel is a partially elastic configuration that can be compressively deformed by the delivery pump, and also is a closed-system configuration with which the fluid flowing inside thereof is isolated from outside.

Further, in order to suppress stirring of the waste fluid separated in the container and to suppress re-mixture thereof with the cultured cells, the delivery system is characterized in that the delivery pump is capable of adjusting a feed speed of the fluid according to a fluid amount inside the one container in a process of feeding the fluid from the one container to the other container.

Furthermore, the delivery system according to the present invention is characterized to include a filter for absorbing fungus/fungi and bacterium/bacteria provided in the middle of the delivery channel of the closed-system configuration.

Moreover, the delivery system is characterized to include a filter for eliminating a foreign matter provided in the middle of the delivery channel of the closed-system configuration.

Advantageous Effects of Invention

According to the present invention, the delivery pump and the fluid delivery tube or the waste fluid container are not directly connected but are simply in contact, so that the container where the waste fluid is accumulated can be moved by simply being detached. Therefore, when handling the waste fluid, it is possible to prevent splashing and the like of the waste fluid onto the workspace.

Further, it is possible with the present invention to suppress occurrence of radical changes in the feed speed of the fluid by the delivery pump even when linear control values are outputted from the controller.

BRIEF DESCRIPTION OF THE DRAWINGS

FIG. 6A is a characteristic chart showing the relation between control values outputted to the delivery pump from the controller and the feed speed of the delivery pump, and FIG. 6B is a characteristic chart showing the relation between the control values outputted to the delivery pump from the controller and the feed speed of the delivery pump used in the embodiment of the present invention;

DESCRIPTION OF EMBODIMENT

Hereinafter, an embodiment of the present invention will be described in details by referring to the accompanying drawings.

Figure 1:
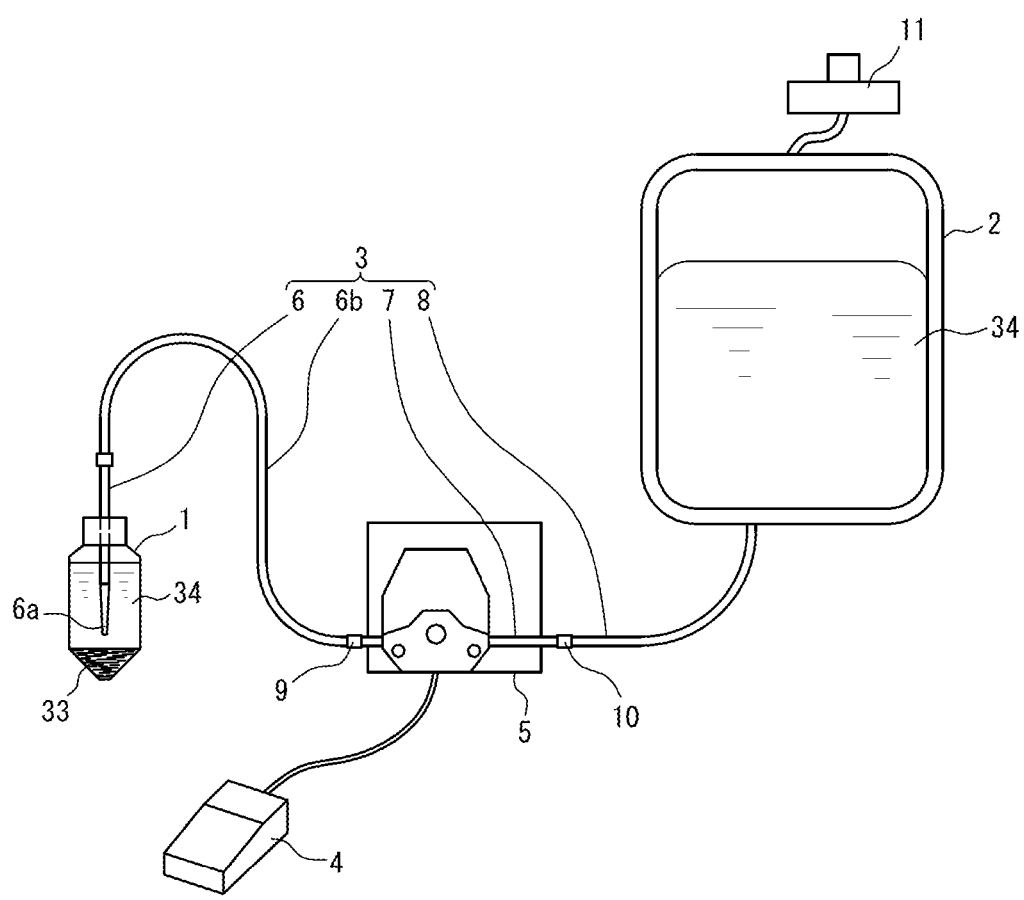
FIG. 1 is a schematic view showing the entire configuration of a fluid delivery system according to an embodiment of the present invention.

As shown in FIG. 1, a fluid delivery system according to an embodiment of the present invention is a fluid delivery system for delivering a fluid from one container 1 to another container 2, which is characterized to include: a delivery channel 3 connecting the container 1 and the other container 2; a controller 4 which controls the feed speed of the fluid linearly; a delivery pump 5 which feeds the fluid into the inside of the delivery channel through compressively deforming the inner diameter in the middle of the delivery channel 3, in which the delivery pump 5 feeds the fluid by giving a margin to the control values of the feed speed outputted from the controller 4.

As shown in FIG. 1, the fluid channel 3 is a closed-system configuration in which the fluid flowing inside thereof is isolated from outside. The configuration will be described in a specific manner.

The delivery channel 3 is formed in a tube-like shape by using a material such as vinyl chloride, for example. In a case shown in FIG. 1, the delivery channel 3 is divided into three. A pipet 6 is disposed on the container 1 side, and the pipet 6 is connected detachably to a delivery tube 7 that is placed at the delivery pump 5. Further, a drainage tube 8 is connected to the delivery tube 7, and the drainage tube 8 is connected to the container 2. Furthermore, a connection point 9 between the pipet 6 and the delivery tube 7 and a connection point 10 between the delivery tube 7 and the drainage tube 8 are formed as a fluid-tight configuration.

As described, the pipet 6, the delivery tube 7, and the drainage tube 8 constituting the delivery channel 3 are connected integrally to form the closed-system configuration in which the inside thereof is isolated from the outside.

The pipet 6 is formed as a configuration in which a tip part 6a to be inserted into the container 1 has a narrow diameter for allowing aspiration easily. A caliber of the tip part 6a of the pipet 6 is set as an appropriate value with which the fluid within the container 1 can be aspirated by corresponding to a negative pressure, to be described later, which is generated within the delivery tube 7 by the delivery pump 5. Further, it is also possible to connect a aspiration tube 6b instead of the pipet 6, prepare the aspiration tubes 6 with various kinds of lengths, and select the proper aspiration tube 6 to aspirate the fluid within the container 1. Alternatively, it is also possible to provide a non-return valve to the pipet 6 and the aspiration tube 6b so as to prevent the aspirated fluid from flowing backward to the container 1 side.

As a mechanism for detachably connecting the pipet 6 and the delivery tube 7, an existing coupler or the like can be used so that explanation of the detailed configuration thereof is omitted. The tip part 6a of the pipet 6 on the container 1 side is formed to have a narrow diameter and a mouth is formed to aspirate the fluid efficiently. The caliber of the mouth is set as appropriate by considering the type of the fluid, the feed speed of the delivery pump 5, and the like.

Next, the delivery tube 7 comes to have its inner diameter compressively deformed along a support face to be described later of the delivery pump 5, so that prescribed thickness and hardness are required. While the outer diameter is set as 6.5 to 11.3 mm and the thickness is set as about 1.6 mm by corresponding to the delivery pump 5 used in the embodiment of the present invention, the numerical values are not limited only to those. The delivery tube 7 is simply required to have the thickness and hardness which can bear the compressive deformation that may be caused by the delivery pump 5.

Further, in the case shown in FIG. 1, a compressive deformation force caused by the delivery pump 5 works on the delivery tube 7 while no compressive deformation force caused by the delivery pump 5 works on the drainage tube 8, so that a configuration divided into the delivery tube 7 and the drainage tube 8 is employed. However, it is also possible to employ the so-called integrated configuration of the delivery tube 7 (including the aspiration tube 6b) and the drainage tube 8 in which the length of the delivery tube 7 is extended and the extended part is used as the drainage tube. Further, an aspiration tube having an equivalent inner diameter may be used instead of the pipet 6 without using the pipet 6. Furthermore, it is also possible to employ a configuration in which the delivery tube 7 is extended, and the tip opening of the extended part is inserted into the fluid in the container 1.

Next, the configuration of the container 2 will be described. In the case shown in FIG. 1, the container 2 is formed with a material exhibiting flexibility. Further, the container 2 includes an air vent filter 11 for preventing rupture caused by the internal pressure.

Figure 2:
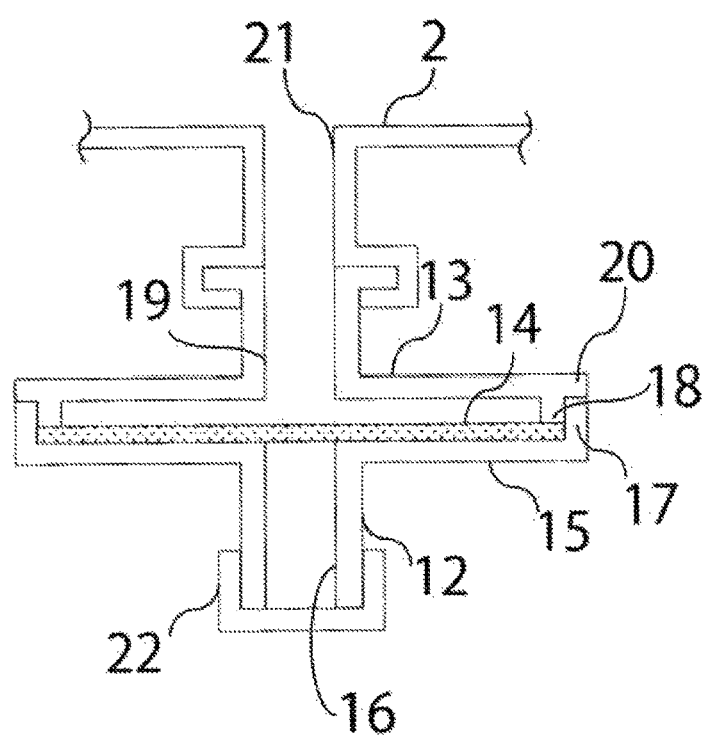
FIG. 2 is a sectional view showing an air vent filter used in the fluid delivery system according to the embodiment of the present invention.

Next, specific configurations of the air vent filter 11 will be described by referring to FIG. 2. As shown in FIG. 2, the air vent filter 11 is formed with a pair of housings 12, 13 and a filter material 14.

One housing 12 mentioned above is formed with a material such as polypropylene, polyethylene, or the like, for example, and includes a pedestal 15 for supporting the fringe part of the filter material 14, and a ventilation path 16 opened in the center of the pedestal 15. Further, the housing 12 includes a ring-like flange 17 projected from the fringe of the pedestal 15.

The other housing 13 is formed with a material such as polypropylene, polyethylene, or the like, for example, and includes a ring-like stay 18 which presses the fringe part of the filter member 14 against the pedestal 15 of the housing 12, and a ventilation path 19 connected to the ventilation path 16 of the housing 12. The other housing 13 includes a ring-like flange 20 in the fringe of the stay 18.

The fluid is delivered into the container 2 by the delivery pump 5 so that the internal pressure of the container 2 becomes higher than the external pressure. Accordingly, there is a difference generated in the pressures on the inner side and the outer side of the filter member 14. Therefore, the air inside the container 2 is exhausted to the outside via the filter member 14 upon receiving the internal pressure of the container 2, and the filter member 14 captures particles contained in the air inside the container 2 to clean the air.

Further, the filter member 14 is formed with hydrophobic polytetrafluoroethylene, for example, and it is configured to pass only gases without passing water and contamination substances (particles) such as aerosol inside the container 2.

Further, the filter member 14 is formed in a mesh configuration such as a nonwoven fabric by using hydrophobic polytetrafluoroethylene or the like, so that the air can be cleaned by letting the air pass through the mesh configuration to capture the particles contained in the air with the fiber. Further, the filter member 14 is formed as a configuration which prevents the fluid inside the container 2 from leaking out of the container when the filter member 14 comes in contact with the fluid inside the container 2 and the mesh configuration becomes clogged by the fluid. That is, the filter member 14 includes a filtering function which cleans the air exhausted to the outside from the container 2, and a function as a non-return valve for preventing the fluid inside the container 2 from leaking out when it comes in contact with the fluid inside the container 2.

The housing 13 is attached to the container 2 integrally under a state where the ventilation path 19 is connected to a ventilation port 21 opened to the container 2.

The housing 12 is combined with the housing 13 by having the ventilation path 16 aligned with the ventilation path 19 of the housing 13. The filter material 14 is placed on the pedestal 15 of the housing 12. Further, the fringe part of the filter material 14 is pressed against the pedestal 15 of the other housing 12 by the ring-like stay 18 of the housing 13, and the flanges 17, 20 of the housings 12, 13 are abutted against each other while keeping that state to assemble a pair of the housings 12, 13 into a unified body. In a state where the housings 12 and 13 as a pair are assembled, the filter material 14 is interposed in the connection point between the ventilations paths 16, 19 of the pair of housings 12, 13. Further, a closing cap 22 is detachably fitted at the ventilation port connecting to the ventilation path 16 of the housing 12.

Figure 3:
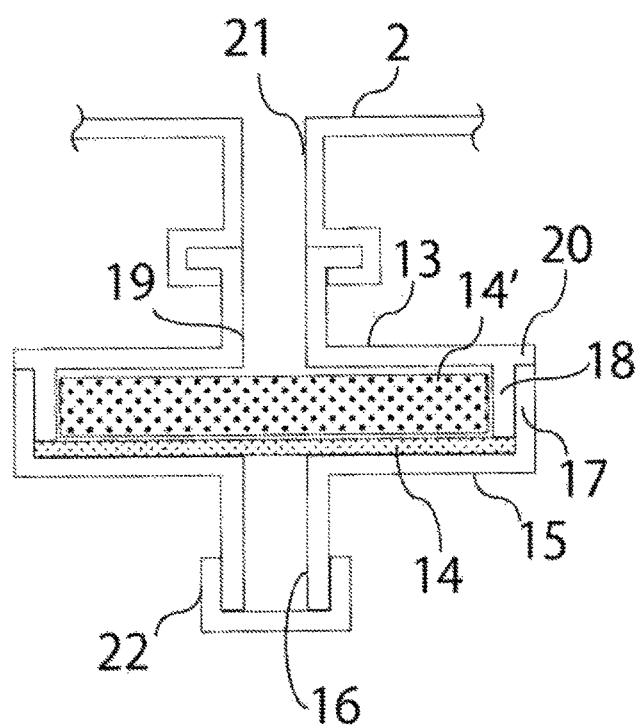
FIG. 3 is a sectional view showing another air vent filter used in the fluid delivery system according to the embodiment of the present invention.

In a case shown in FIG. 2, the filter member 14 is formed as a single-layer configuration. However, as shown in FIG. 3, a filter material 14' may be superimposed on the filter material 14 to have a double-layer configuration so as to improve the filtering function and the non-return valve function. In that case, by using the material with larger pores than the pores of the filter material 14 for the filter material 14' on the side closer to the ventilation path, foreign matters contained in the exhaust can be adsorbed efficiently. Note that the filter material 14 may also be a configuration of more than two layers. Through employing the configuration of more than two layers, the filtering function and the non-return valve function may be improved further.

In the case shown in FIG. 1, the container 2 is formed with a material exhibiting flexibility, so that the delivery channel 3 and the container 2 may be formed as an integrated configuration in a connected state.

It is not required to form the container 2 with a flexible material. A bottle or any other types may be used as long as it is a configuration that can store fluids. It is preferable to use a flexible container such as a waste-fluid bag, for example, since it is easy to form a configuration that can seal the fluid. Further, while the container 1 is formed as a bottle configuration for culturing cells, it is not limited only to such configuration. The container 1 may be formed with a flexible material. The point is that the configuration of the container 1 and the other container 2 may be selected properly by corresponding to the fluid to be delivered.

The fluid delivery system according to the present invention is a fluid delivery system which is characterized in that the delivery pump can adjust the feed speed of the fluid in a process of feeding a fluid from one container to another container according to the remaining amount of the fluid inside the one container.

As a method for adjusting the feed speed, there are a method which places a speed adjusting switch at the delivery pump, a method which adjusts the speed by a foot switch, and the like.

In a case where a speed adjusting switch is placed at the delivery pump, there are a method which places a plurality of buttons and sets rotation speeds of the pump to each of the buttons, a method which places a knob-type switch and the rotation amount and the rotation speed of the pump are associated with each other, and a method which gives a program setting function to the delivery pump and the rotation speed of the pump is changed from start of aspirating a waste fluid along the time passage. Furthermore, there is also a method which measures the amount of the fluid (volume or weight) inside one container by a sensor, and decreases the rotation speed of the pump according to the reduction in the amount of the fluid. These specific examples will be described later.

In a case where the feed speed is adjusted by a footswitch, there are a method which controls the speed linearly by associating the step-on amount and the rotation speed of the pump, a method which switches the actions of "fast", "slow", and "stop" by stepping on the footswitch, for example.

Hereinafter, described as a way of example is a case where the delivery pump employs a footswitch which controls the speed linearly.

Figure 4:
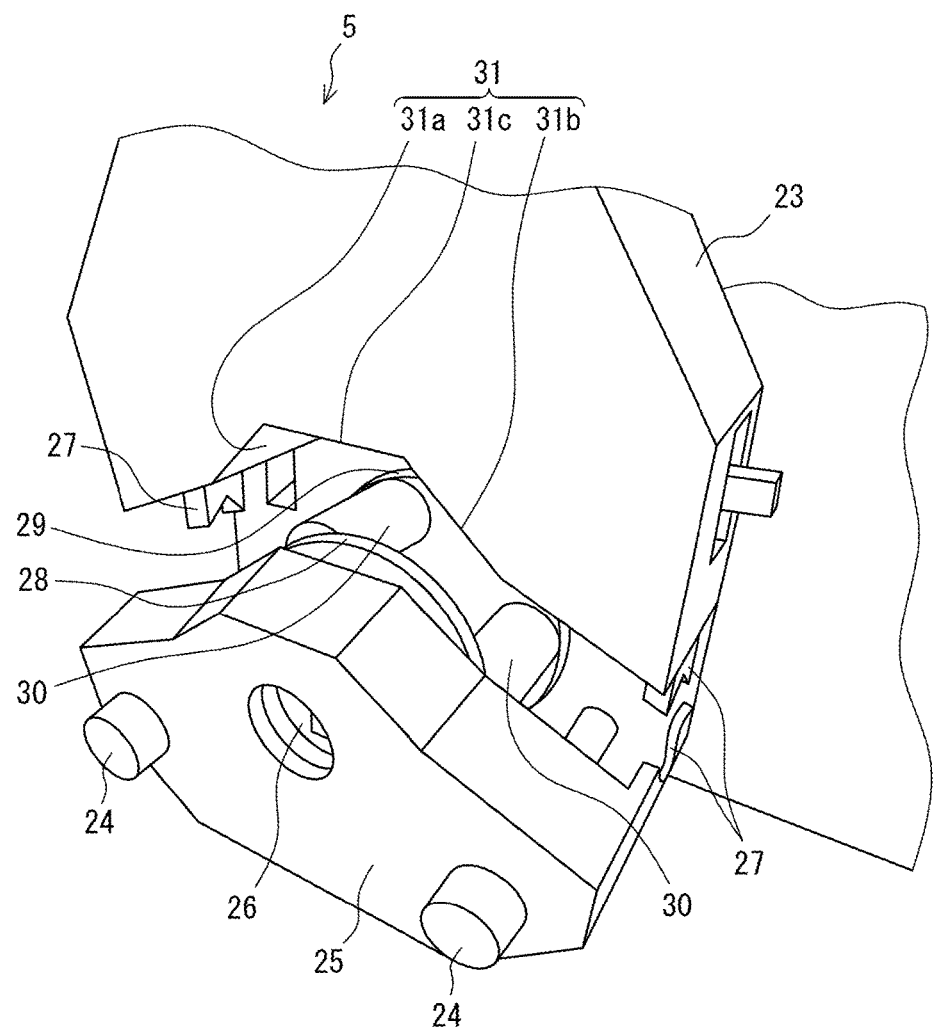
FIG. 4 is a perspective view showing a main part of the fluid delivery pump used in the embodiment of the present invention.
Figure 5:
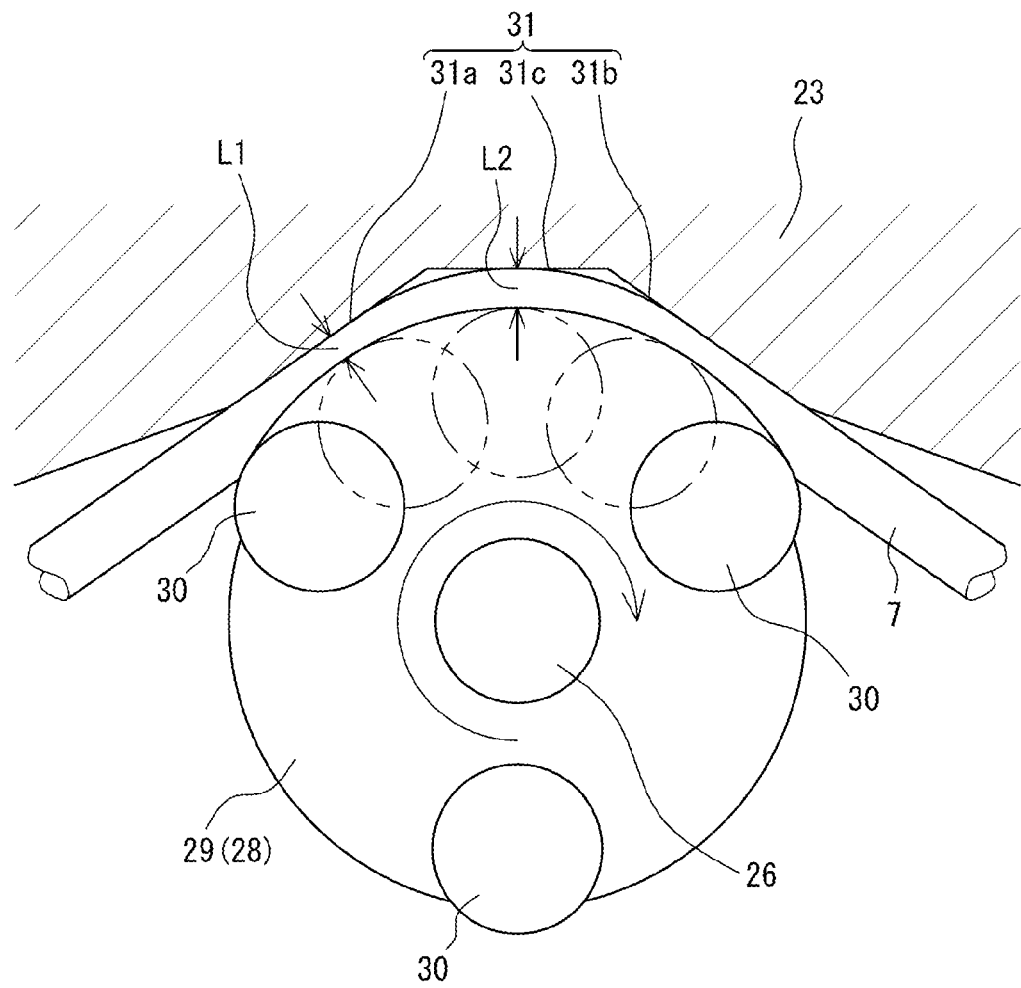
FIG. 5 is a block diagram showing the relation regarding a support face of a delivery pump, a fluid delivery tube of a fluid delivery channel, and rollers used in the embodiment of the present invention.

Next, another specific configuration of the delivery pump 5 will be described. As shown in FIG. 4 and FIG. 5, the delivery pump 5 feeds a fluid by using a pressure difference within the delivery channel 3 through generating a negative pressure inside the delivery channel 3 by compressively deforming the inner diameter somewhere in the middle (particularly the delivery tube 7) of the delivery channel 3. The delivery pump 5 is configured to deliver the fluid with a margin given to the control value when controlling the feed speed outputted from the controller 4.

As shown in FIG. 4, two ledges 24 are attached in front of a pump main body 23 by being kept in parallel, and a bearing 25 is supported to the ledges 24 to be in parallel to the pump main body 23. A shaft 26 supports about the bearing 25 and a bearing, not shown, of the pump main body 23 rotatably in a horizontal posture. The shaft 26 is associated with a driving source, not shown, and the shaft 26 is rotationally driven by the driving source, not shown. The driving source for rotationally driving the shaft 26 has no specific feature, so that no illustration thereof is provided.

Two parallel disks 28, 29 are disposed in parallel to support about the shaft 26 disposed between the pump main body 23 and the bearing 25, and three rollers 30 are disposed in the two disks 28, 29 by being isolated at 120° in the circumferential direction. For attaching the three rollers 30 to the two disks 28, 29, the three rollers 30 are located on a same circle with the shaft 26 being the center. In FIG. 4, only the two rollers 30 are illustrated, and an illustration of the other roller 30 is omitted since it is located on the back side of the bearing 25.

Note that the number of the rollers 30 is not limited to three, and also the attaching positions thereof are not limited to beat an interval of 120° in the circumferential direction.

As shown in FIG. 4 and FIG. 5, a supporting face 31 is provided to the pump main body 23 along a circular orbit the rollers 30 follow. As shown in FIG. 5, the supporting face 31 is formed as a mountain-like shape surface configuration configured with sloping surfaces 31*a*, 31*b* extended in different tangential lines with respect to the circular orbit the rollers 30 follow (i.e., different sloping directions) and a flat surface 31*c* connecting those. The flat surface 31*c* is formed as a linear surface extended in parallel to the tangential direction of the disks 28 and 29. In FIG. 4, reference numeral 27 is a retainer which fixedly holds the both ends of the delivery tube 7 disposed along the supporting face 31.

The container 1 side of the delivery tube 7 of the delivery channel 3 is placed along the sloping surface 31*a* of the supporting face 31, the container 2 side thereof is placed along the sloping surface 31*b* of the supporting face 31 and, further, the center part thereof is placed along by being bent in an arc shape.

In that case, the flat surface 31*c* of the supporting face 31 forms a linear shape and the center part is bent in an arc shape due to its flexibleness. Therefore, the center part of the delivery tube 7 is not completely placed along the linear flat surface 31*c* of the supporting face 31 but is placed by keeping a gap between with the both ends of the flat surface 31*c* of the supporting face 31. The positional relation between the center part of the delivery tube 7 and the flat surface 31*c* of the supporting face 31 provides an effect of giving a margin to the control values from the controller 4. This will be described later.

Therefore, the controllers 30 come to face each other with the delivery tube 7 placed along the supporting face 31, and the delivery tube 7 is pressurized by the sloping surfaces 31*a*, 31*b* and the flat surface 31*c* of the supporting face 31 in the circumferential face of the rollers 30 according to the rotation of the disks 28, 29. Thereby, the inner diameter of the delivery tube 7 is compressively deformed by the pressure applied by rollers 30 on the delivery tube 7, which generates a negative pressure for aspirating the fluid inside the container 1. The three rollers 30 pressurize the delivery tube 7 sequentially in accordance with the rotation of the disks 28, 29 in the delivery direction to compressively deform the inner diameter. Thereby, the fluid inside container 1 is delivered to the container 2.

Note that the detailed configuration for compressively deforming the inner diameter of the delivery tube 7 by the rollers 30 in the delivery pump 5 is mentioned in Patent Literature 2, and there is no specific feature in that configuration. There is a specific feature in the positional relation between the rollers 30 and the supporting face 31 for compressively deforming the inner diameter of the delivery tube 7 by the rollers 30 in the embodiment, so that the configuration thereof is focused in the explanation of the embodiment described above.

The controller 4 is designed to transmit the control values that linearly change the feed speed of the fluid to be delivered by the delivery pump 5 to the driving source of the delivery pump 5. In the embodiment, used as the controller 4 is the footswitch that linearly changes the control values for controlling the speed in proportion to the step-on amount by foot.

(Delivery Actions by Fluid Delivery System According to Embodiment)

Next, described is a case where the delivery pump according to the embodiment is used when discarding a waste fluid after being used for cell culture (referred to as a waste fluid hereinafter) through delivering the fluid from the container 1 used for the cell culture to the waste fluid housing container 2.

In the cell culture, cells are cultured in a fluid to be a culture medium. When separation is done by settling, centrifugation, or the like after the culture, cultured cells 33 precipitated on the bottom part inside the container 1 and a fluid 34 (written as a waste fluid hereinafter) of the used medium as supernatant are separated on top and bottom. In order to shift to a next work step from the state where the cultured cells 33 in the container 1 are separated, it is necessary to discard the waste fluid 34 as the supernatant. When discarding, it is necessary to make sure that the cultured cells 33 and the waste fluid 34 are not mixed again in the process of the discarding the waste fluid 34 from the container 34, i.e., it is necessary to prevent the waste fluid 34 from ruffling, for example.

The pipet 6 of the delivery channel 3 is inserted into the waste fluid 34 in the container 1, and the control value for controlling the speed is inputted to the delivery pump 5 from the controller 4 to drive the delivery pump 5.

When the delivery pump 5 is driven, the rollers 30 revolve around the shaft 26. Thereby, the rollers 30 pressurize the delivery tube 7 placed along the supporting face 31 and compressively deform the inner diameter of the delivery tube 7. While deforming the inner diameter, the rollers 30 shift the compressively deformed state of the delivery tube 7 to the fluid delivering direction along the sloping surface 31a, the flat surface 31c, and the sloping surface 31b of the supporting face 31.

When the inner diameter of the delivery tube 7 is compressively deformed by being pressurized by the rollers 30, there is a pressure change generated inside the delivery channel 3 between the container 1 and the other container 2. Based on the pressure change, the waste fluid 34 inside the container 1 is sent out toward the container 2 side.

Since the inner diameter of the delivery tube 7 is compressively deformed by the three rollers 30 switched sequentially, the above-described actions are continuously executed to feed the waste fluid 34 in the container 1 to the other container 2. When the remaining amount of the waste fluid 34 in the container 1 becomes small, it is required to adjust the feed speed of the delivery pump 5 by the controller 4.

However, the control values for controlling the feed speed are outputted linearly from the controller 4 to the feed pump 5, so that the feed speed of the delivery pump 5 corresponds to the control values from the controller 4 on one-on-one basis. Thus, under a circumstance where the waste fluid 34 is discarded and the remaining amount thereof becomes small so that the aspiration port of the delivery pump 5 (e.g., the aspiration port of the pipet 6) becomes close to the cultured cells 33, there may be a radical change generated in the aspiration speed on the aspiration port side of the delivery pump 5, which may ripple the waste fluid 34 and agitate the cultured cells 33. This results in imposing an influence upon the cultured cells 33.

The embodiment has a specific feature in the configuration with which such phenomenon is suppressed. This will be described in a specific manner.

As shown in FIG. 5, in the delivery pump 5 of the embodiment, the rollers 30 pressurize the delivery tube 7 against the sloping surface 31a of the supporting face 31 from the top end side toward the bottom end side of the sloping surface 31a of the supporting face 31 to compressively deform the inner diameter of the delivery tube 7.

Further, while pressurizing the delivery tube 7, the rollers 30 move from a position facing with the sloping surface 31a to a position facing with the flat surface 31c via the delivery tube 7 as shown by an alternate short and long dashed line.

As described above, the flat surface 31c of the supporting face 31 forms a linear shape, and the center part of the delivery tube 7 is bent in an arc form due to its flexibleness. Therefore, the center part of the delivery tube 7 is not completely placed along the linear flat surface 31c of the supporting face 31. Thereby, a gap is formed between the center part of the delivery tube 7 and the both ends of the flat surface 31c of the supporting face 31.

Comparing the process where the rollers 30 pressurize the center part of the delivery tube 7 against the flat surface 31c of the supporting face 31 with the process where the rollers 30 pressurize the delivery tube 7 against the sloping surface 31a (or the sloping surface 31b) of the supporting face 31, followings can be found.

The sloping surface 31a and the sloping surface 31b of the supporting face 31 are sloping in a tangential direction of the circular orbit along which the rollers 30 rotate. However, the flat surface 31c of the supporting face 31 is in a linear form while being distant from the circular orbit. Therefore, there is a difference between a compressive deformation amount L1 of the delivery tube 7 generated by pressuring the delivery tube 7 against the sloping surface 31a (or the sloping surface 31b) by the rollers 30 and a compressive deformation amount L2 of the delivery tube 7 generated by pressurizing the delivery tube 7 against the flat surface 31c by the rollers 30 (L1>L2).

It is considered that a difference generated in the amount of the compressive deformation of the delivery tube 7 done by the rollers 30 described above (L1>L2) generates a change in the internal pressure of the delivery tube 7 facing the flat surface 31c of the supporting face 31 and the internal pressure of the delivery tube 7 facing the sloping surface 31a (or the sloping surface 31b) and that the so-called play is generated due to the change in the pressure, thereby giving a margin to the control values from the controller 4.

In a case where a footswitch is used as the controller 4, experiences and skills are required for continuously (i.e., linearly) changing the footswitch 4 to continuously (i.e., linearly) change the speed of the delivery pump 5. Thus, when an inexperienced person operates the footswitch 4, there is variation generated in the step-on amount. Thereby, discontinuity is generated in the change in the speed of the delivery pump 5, which ripples the waste fluid 34 inside the container 1.

However, in a case where the fluid delivery system according to the embodiment shown in FIG. 1 is used and the remaining amount of the waste fluid 34 becomes small, it is considered that such phenomenon of rippling the waste fluid 34 inside the container 1 does not occur even when an inexperienced person discontinuously operates the footswitch 4 (controller) by a foot operation.

The reason thereof is considered that a difference generated in the amount of the compressive deformation of the delivery tube 7 done by the rollers 30 described above (L1>L2) generates a change in the internal pressure of the delivery tube 7 facing the flat surface 31c of the supporting face 31 and the internal pressure of the delivery tube 7 facing the sloping surface 31a (or the sloping surface 31b) and that the so-called play is generated due to the change in the pressure, thereby giving a margin to the control values from the controller 4.

This will be described as follows by referring to FIG. 6.

In FIG. 6A, the lateral axis shows the control values, while the longitudinal axis shows the feed speed of the delivery pump. In FIG. 6B, the lateral axis shows step-on amount of the footswitch 4 pressed by foot.

As shown in FIG. 6A, the footswitch 4 as the controller outputs the control value 35 that changes linearly for controlling the feed speed of the delivery pump 5. The step-on amount (the control value) of the footswitch 4 and the feed speed of the delivery pump 5 correspond on one-on-one basis, and there is such a relation that the speed change in the delivery pump 5 becomes discontinuous when the step-on amount of the footswitch 4 is discontinuous. In order to overcome such phenomenon, it is necessary to provide a control circuit between the footswitch 4 and the delivery pump 5 for giving a margin to the speed change, i.e., for giving a margin to the linear control values of the footswitch 4.

In the embodiment, a difference generated in the amount of the compressive deformation of the delivery tube 7 done by the rollers 30 (L1>L2) due to the relation between the supporting face 31 and the rollers 30 generates a change in the internal pressure of the delivery tube 7 facing the flat surface 31c of the supporting face 31 and the internal pressure of the delivery tube 7 facing the sloping surface 31a (or the sloping surface 31b), and the so-called play is generated due to the change in the pressure, thereby giving a margin to the control values from the controller 4.

The fact that delivery pump 5 in the embodiment is designed to deliver the fluid by giving a margin to the control values from the footswitch 4 will be described by referring to FIG. 6B.

In FIG. 6A, when the footswitch 4 outputs the control value 35 pinpoint, it is considered with the embodiment that the feed speed of the delivery pump 5 changes in a very small range that is within a range of a margin H because the margin H is given to the pinpoint control value 35 even when a difference is generated in the amount of the compressive deformation of the delivery tube 7 done by the rollers 30 due to the relation between the supporting face 31 and the rollers 30 (L1>L2) and the so-called play is generated in accordance with a change in the internal pressure of the delivery tube 7 facing the flat surface 31c of the supporting face 31 and the internal pressure of the delivery tube 7 facing the sloping surface 31a (or the sloping surface 31b) so that the step-on amount of the footswitch 4 becomes discontinuous as shown in FIG. 6B.

It is considered that the margin H given to the pinpoint control value 35 changes in accordance with the difference generated in the amount of the compressive deformation of the delivery tube 7 done by the rollers 30 due to the relation between the supporting face 31 and the rollers 30 (L1>L2), i.e., in accordance with the so-called play generated according to the change in the internal pressure of the delivery tube 7 facing the flat surface 31c of the supporting face 31 and the internal pressure of the delivery tube 7 facing the sloping surface 31a (or the sloping surface 31b).

As described above, even when the linearly changing control value 35 is outputted to the delivery pump 5 from the controller 4, it is considered with the embodiment that there is no pulsating motion generated on the pipet 6 side of the delivery channel 3 and the waste fluid 34 reduced to a small remaining amount is not rippled, so that the waste fluid 34 inside the container 1 can be discarded to the other container 2 while securely separating the cultured cells 33 on the bottom part and the supernatant waste fluid 34 inside the container 1. That is, it is considered that the delivery pump 5 is a configuration which delivers the fluid while giving a margin to the control values for controlling the feed speed outputted from the controller 4.

After transferring the waste fluid 34 from the container 1 to the other container 2, the waste fluid 34 is prevented from leaking out to the outside by heat-sealing the aspiration tube 6b and the drainage tube 8. Thereafter, the delivery channel 3 and the container 2 are discarded while being kept in an integrated body.

In the above, described is the case where the fluid delivery system according to the embodiment is used for delivering the waste fluid 34 that is generated after cell culture. However, the use of the fluid delivery system is not limited only to such case.

Further, while the delivery pump 5 of a single type which delivers a fluid via a single delivery channel 3 by using a single delivery pump 5 is described in the embodiment, it is also possible to employ a configuration with which the single-type delivery pumps 5 are disposed in a multiple manner and a plurality of kinds of fluids are delivered simultaneously through a plurality of delivery channels 3.

In the embodiment, described above is the case where the feed speed of the fluid by the delivery pump is made adjustable by using the footswitch as the controller according to the remaining amount of the fluid in the container in a process of feeding the fluid from the container to the other container. A specific configuration for adjusting the feed speed of the fluid by the delivery pump of another case will be described by referring to the drawings.

Figure 7A:
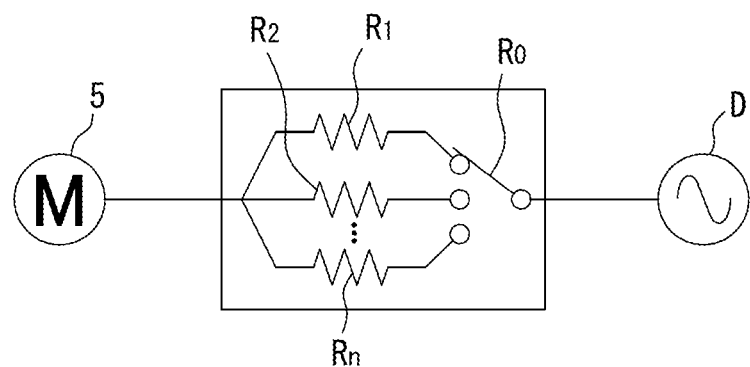
FIG. 7 is a block diagram showing a configuration which makes it possible to adjust the feed speed of the fluid by the delivery pump according to the remaining amount of the fluid in one container in a process of feeding the fluid from that container to another container in the present invention.
Figure 7B:
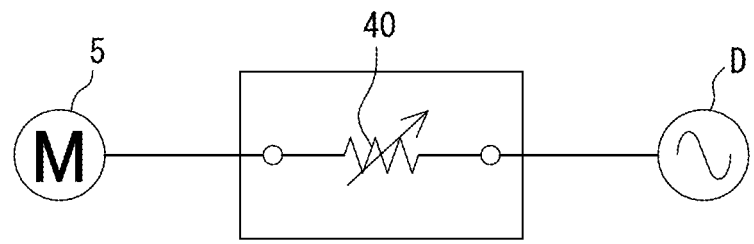

FIGS. 7A and 7B show examples of a case where a speed adjusting switch is placed at the above-described delivery pump.

In the example shown in FIG. 7A, a plurality of resistances R1, R2, - - - , Rn with different resistance values are disposed in parallel on the input side of the delivery pump 5, one of the plurality of resistances R1, R2, - - - , Rn is selected by a switching terminal R0, and an electric current supplied from a power source D to the delivery pump 5 is adjusted by the resistance value of the resistance to adjust the feed speed of the fluid by the delivery pump 5.

In the above example, the delivery pump 5 is in an analog configuration. However, it is also possible to employ a digital configuration as the delivery pump which is driven by pulse signals from the power source D, and the feed speed of the fluid by the delivery pump 5 is adjusted by changing the frequency of the pulse supplied from the power source D.

In the example shown in FIG. 7B, a variable resistor 40 is connected between the delivery pump 5 and the power source D, the electric current value supplied to the delivery pump 5 from the power source D is adjusted through adjusting the resistance value of the variable resistor 40 by corresponding to a rotation amount of a knob-type switch of the variable resistor 40 so as to adjust the feed speed of the fluid by the delivery pump 5.

Figure 8:
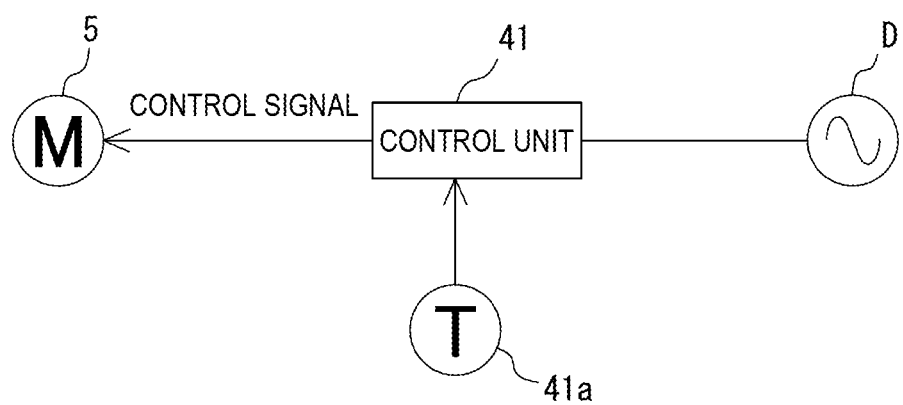
FIG. 8 is a block diagram showing a configuration which makes it possible to adjust the feed speed of the fluid by the delivery pump according to the remaining amount of the fluid in one container in a process of feeding the fluid from that container to another container in the present invention.

An example shown in FIG. 8 is a case where a control unit 41 is connected between the delivery pump 5 and the power source D, and a timer 41a is built-in to the control unit 41. A program designed to adjust the feed speed of the fluid by the delivery pump 5 as the time passes from the start of aspirating the waste fluid is set to the control unit 41, and the feed speed of the delivery pump is decreased gradually based on the time information counted by the timer 41a to suppress generation of radical changes in the feed speed of the fluid by the delivery pump.

The example shown in FIG. 7 is the case where the operator artificially changes the feed speed of the delivery pump 5 while observing the remaining amount of the waste fluid 34 in the container 1. However, it is also possible to associate the remaining amount of the waste fluid and the feed speed of the delivery pump 5. Further, the example of FIG. 8 is a case where the feed speed of the delivery pump 5 is adjusted based on the time information counted by the timer 41a. However, it is also possible to adjust the feed speed of the delivery pump 5 by combining the time information counted by the timer 41a and the waste fluid remaining amount information.

Figure 9:
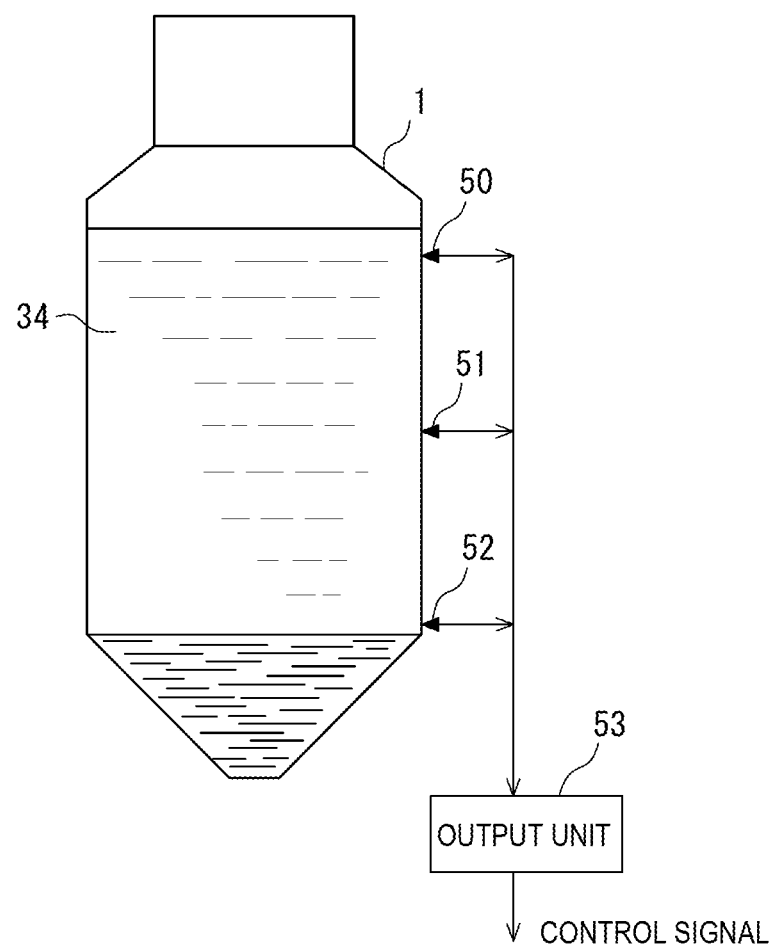
FIG. 9 is a block diagram showing an example of measuring the remaining amount of a waste fluid within a container is measured.

FIG. 9 shows an example of measuring the remaining amount of the waste fluid 34 in the container 1, in which a sensor 50 for measuring an upper limit value within the container 1, a sensor 51 for measuring a threshold value, and a sensor 52 for measuring a lower limit value are provided, and an output unit 53 which outputs the output values of the sensors 50, 51, and 52 as speed information is provided.

The output unit 53 is configured to output a control signal for setting the feed speed of the delivery pump 5 as a normal speed during a period from a point at which a measurement signal from the sensor 50 is received until a point at which a measurement signal form the next sensor 51 is received, to output a control signal for gradually decreasing the normal speed of the delivery pump 5 upon receiving a measurement signal from the sensor 51, and to output a control signal for stopping the delivery pump 5 upon receiving a measurement signal from the sensor 52.

While the example shown in FIG. 9 is a case of measuring the remaining amount inside the container 1 by measuring the volume inside the container 1, it is also possible to measure the remaining amount inside the container 1 by measuring the weight of the container 1 including the waste fluid 34. In this example, the output unit 53 outputs control values corresponding to the measurement values of the sensors 50, 51, and 52 in accordance with the weight of the container 1 measured by a gravimeter.

In a case where the example of FIG. 9 is combined with the example of FIG. 7, one of the plurality of resistances R1, R2, - - - , Rn is selected by the switching terminal R0 by corresponding to the control signal from the output unit 53, and the feed speed of the delivery pump is adjusted linearly by corresponding to the remaining amount of the waste fluid within the container 1 instead of selecting the resistances R1 to Rn artificially.

In a case where the example of FIG. 9 is combined with the example of FIG. 8, the feed speed of the delivery pump is adjusted linearly by corresponding to the remaining amount of the waste fluid within the container 1 by a combination of the control signal from the output unit 53 of FIG. 9 and a clocking signal from the timer 41a.

While the configuration capable of adjusting the feed speed of the fluid by the delivery pump according to the remaining amount of the fluid within one container in a process of feeding the fluid from the container to another container is described, the configuration is not limited only to that. Any other configurations may be employed as long as the configurations are capable of adjusting the feed speed of the fluid by the delivery pump according to the remaining amount of the fluid within one container in a process of feeding the fluid from the container to another container.

Further, it is also possible to employ a configuration which adjusts the feed speed of the fluid by the delivery pump according to the fluid amount inside the other container. For example, there is a method which starts to measure the fluid amount in the other container at a point where aspiration of the fluid is started by the delivery pump, and decreases the feed speed when a specific amount is increased. In that case, instead of the container of FIG. 9, the sensors 50, 51, and 52 measure the fluid amount within the other container and the output unit 53 transmits a control signal by corresponding to the measured value.

Further, it is also possible to employ a configuration which adjusts the feed speed of the fluid by the delivery pump according to the fluid amount passed through the delivery tube. There is a method which measures the fluid transferred from one container to another container and adjusts the feed speed by the delivery pump according to the fluid amount.

As described above, the embodiment of the present invention is the fluid delivery system for delivering a fluid from one container to another container, which includes: the delivery channel connecting the container to the other container and the delivery pump for feeding the fluid inside the delivery channel through compressively deforming the inner diameter in the middle of the delivery channel. The delivery channel is a configuration in which a part thereof exhibits elasticity that can be compressively deformed by the delivery pump and also a closed-system configuration with which the fluid flowing inside thereof is isolated from outside. Therefore, it is possible with the embodiment of the present invention to provide the fluid delivery system configured to avoid contamination of the workspace by splashing and the like of the waste fluid. Further, the delivery pump and the delivery tube or the waste fluid container are not directly connected but are simply in contact, so that the container for accumulating the waste fluid can be moved by simply being detached. Therefore, splashing and the like of the waste fluid onto the workspace can be prevented.

Furthermore, since the delivery pump according to the embodiment of the present invention is configured to feed the fluid by giving a margin to the control values for controlling the feed speed outputted from the controller, it is possible to suppress generation of radical changes in the feed speed of the fluid by the delivery pump even when linear control values are outputted from the controller.

Moreover, the delivery pump according to the embodiment of the present invention is configured as the configuration which includes: a supporting face formed by two connected surfaces of different sloping directions along which the middle of the delivery channel is placed; and a head which pressurizes the middle of the delivery channel placed along the supporting face and shifts the pressurized state to the fluid delivering direction. Thereby, the inner diameter of the delivery tube is compressively deformed and the so-called play is generated, so that the margin of the control values for controlling the feed speed can be adjusted as appropriate.

Further, the delivery channel according to the embodiment of the present invention is a closed system with which the fluid flowing inside thereof is isolated from the outside. Therefore, the fluid delivery from the container having the waste fluid therein, which requires to prevent external diffusion of the culture fluid and the like used for cell culture, can be done inside the closed system. Thereby, external diffusion can be prevented.

Further, the other container includes an air vent filter for suppressing increase in the internal pressure thereof, so that it is possible to suppress increase in the pressure within the other container even if a gaseous body mixed in the fluid is aspirated by the delivery pump and flows into the other container. Therefore, even when the container exhibits flexibility, the container can be prevented from bursting.

Furthermore, the air vent filter is for blocking circulation of the fluid within the other container toward the outside by being in contact with the fluid. Therefore, by simply having the fluid within the other container in contact with the air vent filter, the air vent filter can function as a non-return valve.

Through detachably providing a pipet to the delivery channel on the container side from which the fluid to be delivered, it is possible to exchange and mount the pipets with various kinds of different calibers of the aspiration ports. Further, the pipet that has touched a solvent can be exchanged by each operation, so that the risk of contamination or the like between samples (cross contamination) can be decreased.

Furthermore, since no pulsation transmitting within the delivery channel is generated by the delivery pump, the length of the delivery channel between the delivery pump and the container and the length between the delivery pump and the other container can be changed variously. This makes it possible to aspiration the fluid from the container without a pipet by extending the length of the delivery channel on that container side.

In general, speed control of the delivery pump is done by an analog dial that is provided to the delivery pump. However, with such configuration, one of the hands of the operator is restrained for the speed control operation. With the embodiment, however, speed control of the delivery pump can be done by a footswitch operated by foot. Therefore, the operator can execute a fluid delivery operation by both hands while controlling the speed of the delivery pump by foot.

The footswitch controls the feed speed of the fluid linearly, and the delivery pump under such control reacts sensitively to the speed control done by the footswitch. More experiences and skills are required with the operation by foot than the operation by hand for conducting linear operations.

However, the embodiment employs the configuration with which the delivery pump delivers the fluid with a margin given to the control values for controlling the feed speed outputted from the controller, so that it is possible to suppress generation of radical changes in the feed speed of the fluid by the delivery pump even when the linear control values are outputted from the controller. This enables unskilled operators to smoothly adjust the feed speed of the delivery pump even when using the footswitch.

Further, since the delivery pump is used by integrating the delivery channel and the other container in a connected state, the container can be discarded without cutting the connection at the connection point between the delivery tube, the waste fluid container, and the like when discarding the container. Therefore, after the waste disposal, the surroundings are not contaminated. In particular, a risk of contaminating the surroundings can be decreased further through sealing the inlet part of the waste fluid container by heat sealing or the like.

Furthermore, through providing a non-return valve in the middle of the delivery channel from the container to the other container, it is possible to prevent the fluid transferred to the other container from flowing backward and leaking to the outside.

Furthermore, through connecting a sterility test kit at a connection point between the delivery channel and the other container and connecting another container after the sterility test kit, a solution can be separated into the sterility test kit easily. This makes it possible to conduct a sterility test easily.

Through connecting a container having antiseptic inside thereof instead of the sterility test kit and delivering a fluid to another container via the container with the antiseptic, it is possible to execute inactive treatment of infectious microbes, viruses, and the like within the other container.

Through using a container capable of autoclaving as the other container, waste fluid processing can be conducted extremely easily.

In the field of regenerative medicine, the sterility test is considered as an essential quality test item. While the fluid delivery system according to the present invention delivers a solution from one container to another container by employing a closed-system configuration, it is possible to take out the fluid delivered by the fluid delivery system as a sample for performing a sterility test under a state where the influences of external environments are eliminated by mounting the sterility test kit into the closed-system configuration. Hereinafter, the configuration of the sterility test kit within the above-described fluid delivery system will be described.

For conducting the sterility test of the fluid delivered by the fluid delivery system, there is a method which conducts the sterility test by using a membrane filter. More specifically, there is a method which filtrates a sample or a sample solution by using a membrane filter, cultures the membrane filter by placing it in a medium, and judges existence of viable cells according to existence of growth in fungus/fungi and bacterium/bacteria.

For this method, the solution for the sterility test can be taken out through delivering the solution by connecting the sterility test membrane filter to the delivery channel 3, for example.

Figure 10:
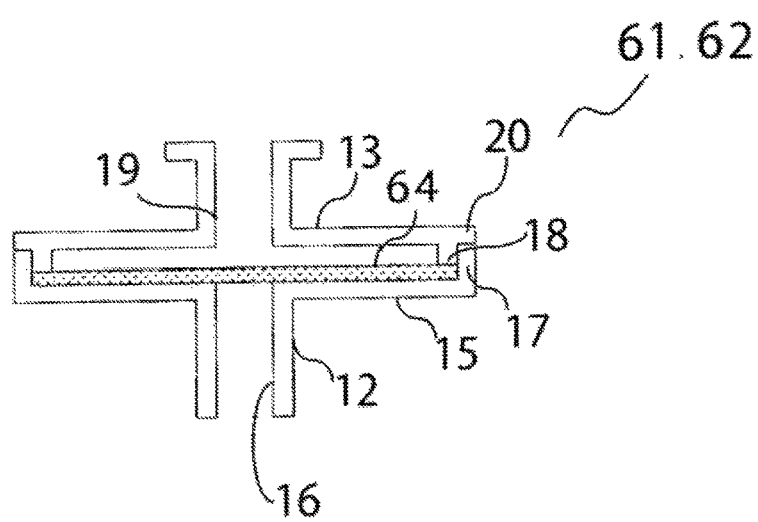
FIG. 10 is a sectional view showing a sterility test membrane filter used in the fluid delivery system according to the embodiment of the present invention.

FIG. 10 shows an example of the above-described sterility test membrane filter used in the present invention. Sterility test membrane filters 61 and 62 shown in FIG. 10 are in a configuration similar to that of the air vent filter 11 shown in FIG. 2. However, a filter member 64 used for forming the sterility test membrane filters 61 and 62 shown in FIG. 10 is formed by a material through which a fluid can pass but fungus/fungi and bacterium/bacteria cannot pass, such as mixed cellulose ester or the like. Note that explanations of the configurations to which a same reference sign as that of the air vent filter 11 is applied are omitted.

Next, described by referring to FIG. 11 to FIG. 14 is an example of taking an aseptic solution flowing within the delivery channel while eliminating the influences of external environments by using the sterility test membrane shown in FIG. 10.

Figure 11:
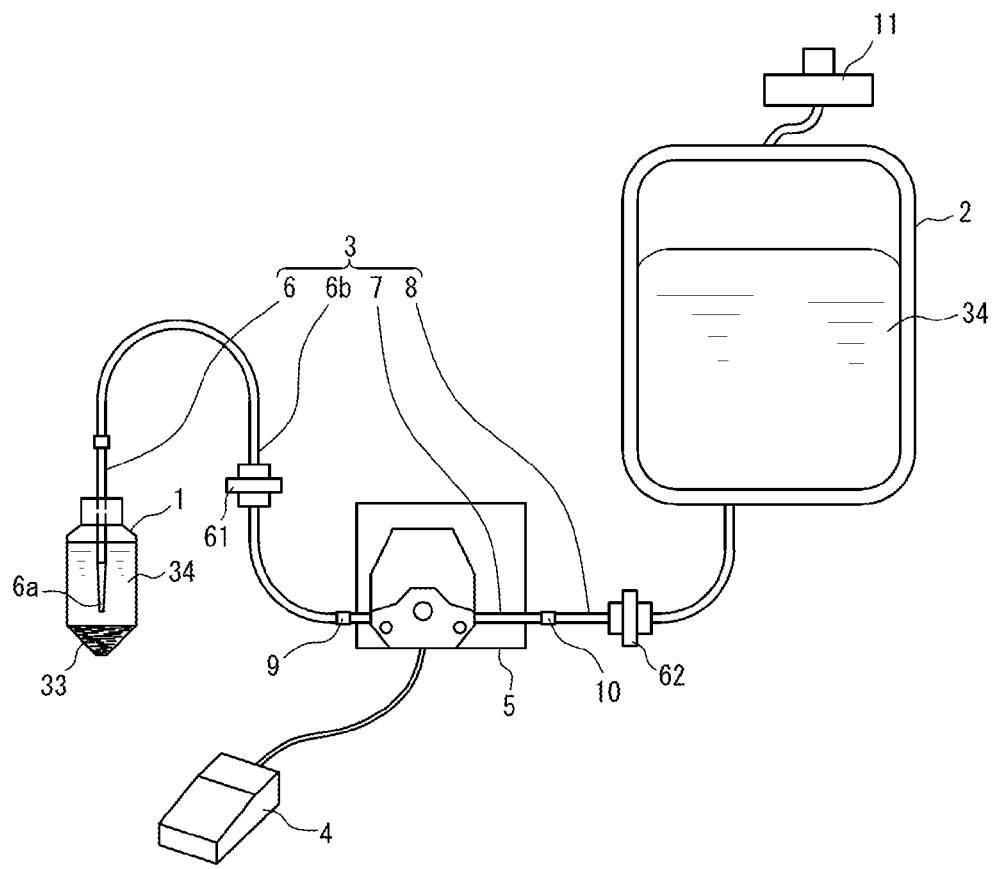
FIG. 11 is a schematic view showing an example where the sterility test membrane filter is placed in the fluid delivery tube and a drainage tube according to the present invention.

An example shown in FIG. 11 is a configuration in which the sterility test membrane filter 61 is mounted in the middle of the aspiration tube 6b on the inlet side of the delivery pump 5 and the sterility test membrane filter 62 is mounted in the middle of the drainage tube 8 on the outlet side of the delivery pump 5.

In a case where fungus/fungi and bacterium/bacteria exist in the fluid to be delivered in the example shown in FIG. 11, the fungus/fungi and bacterium/bacteria are adsorbed by the sterility test membrane filter 61 in a previous stage of the delivery pump 5 and also absorbed by the sterility test membrane filter 62 at a later stage of the delivery pump 5.

In order to extract the fungus/fungi and bacterium/bacteria captured by the sterility test membrane filters 61,62 from the delivery channel 3 of the closed-system configuration, the tubes before and after the sterility test membrane filters 61, 62 are sealed by heat sealing or the like and taken out after delivery of the fluid is completed, the filter member 64 is detached from the sterility test membrane filters 61,62 and laminated to a separate container having a culture medium placed therein, and it is placed in an incubator for the sterility test to execute incubation. Further, when the housing 13 covering the sterility test membrane filter is a configuration to which a culture medium can be applied directly within the container, it is possible to apply the culture medium to the sterility test membrane filters 61, and then place those directly in the incubator to execute incubation. Therefore, the sterility test can be conducted while keeping the closed-system configuration of the present invention.

Note that FIG. 11 shows the configuration in which the sterility test membrane filters 61 and 62 are placed at two points of the aspiration tube 6b and the drainage tube 8. This is an Example for checking whether or not both of the aspiration tube 6b and the drainage tube 8 are maintained in a sterile state. For simply conducting the sterility test of the waste fluid only, it is sufficient to place either one of the sterility test membrane filters 61 and 62.

In the above, the case of placing the membrane filter in the fluid delivery system of the present invention in order to take a sample for the sterility test is described as an example. However, the same mode can be used also in a case where the membrane filter is placed in order to eliminate fungus/fungi and bacterium/bacteria from the solution to be delivered.

Figure 12:
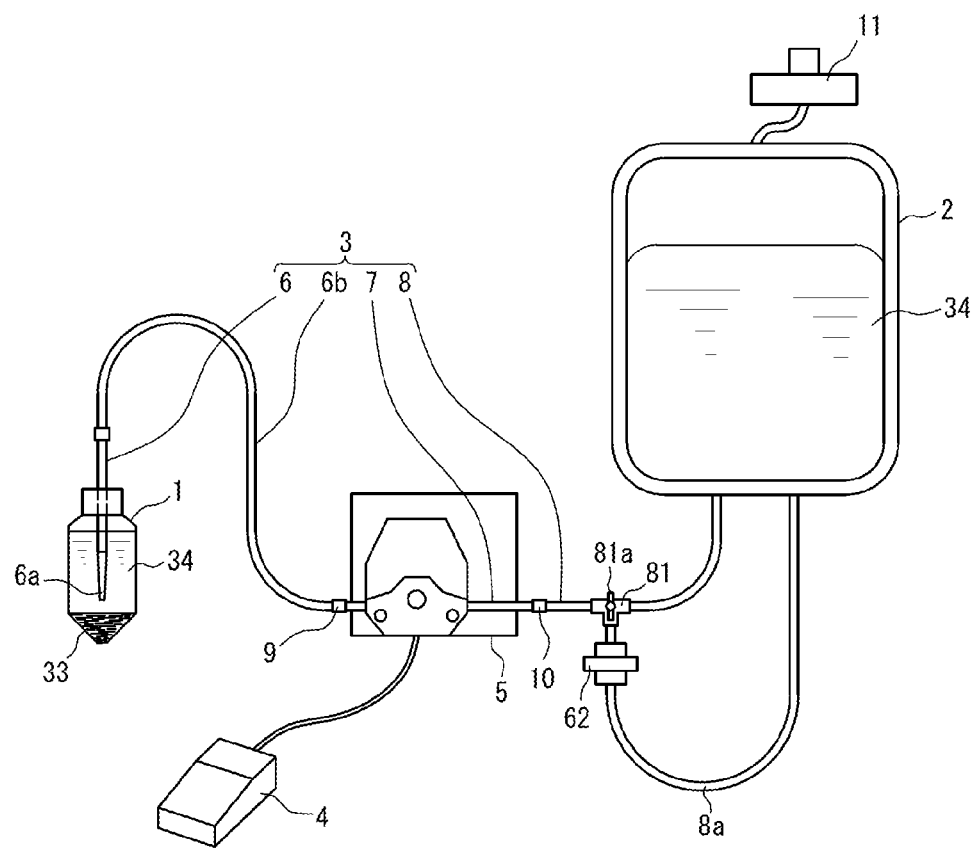
FIG. 12 is a schematic view showing an example where the sterility test membrane filter is placed in the fluid delivery tube and a drainage tube according to the present invention.

The example shown in FIG. 12 is a configuration in which the sterility test membrane filter 62 is placed on the delivery channel 3 via a three-way stopcock 81.

In the example shown in FIG. 12, it is possible to select the flow channel for delivering the fluid between a flow channel going through the sterility test membrane filter 62 and a flow channel directly reaching the container 2 without going through the sterility test membrane filter 62.

As shown in FIG. 12, when it is possible to select the flow channels of the fluid from the two kinds of flow channels, the amount of fluid passing through the sterility test membrane filter 62 can be adjusted. Thus, only the amount of the sample (fluid) required for the sterility test can be let through the filter member.

FIG. 12 shows a state where a cock 81a selects the flow channel on the sterility test membrane filter 62 side. In that state, the fluid filtered by the sterility test membrane filter 62 is fed to the container 2 through a drainage bypass 8a. Therefore, the sterility test can be conducted while maintaining the closed-system configuration of the present invention. The cock 81a is operated to feed the fluid to the container 2 via the drainage tube 8 at a stage where filtration of the amount of the sample (fluid) required for the sterility test is completed. Thereby, the sterility test can be conducted while maintaining the closed-system configuration. Note that it is also possible to connect the drainage bypass 8a to another container (not shown) and feed the fluid filtered by the sterility test membrane filter 62 to that container.

Figure 13A:
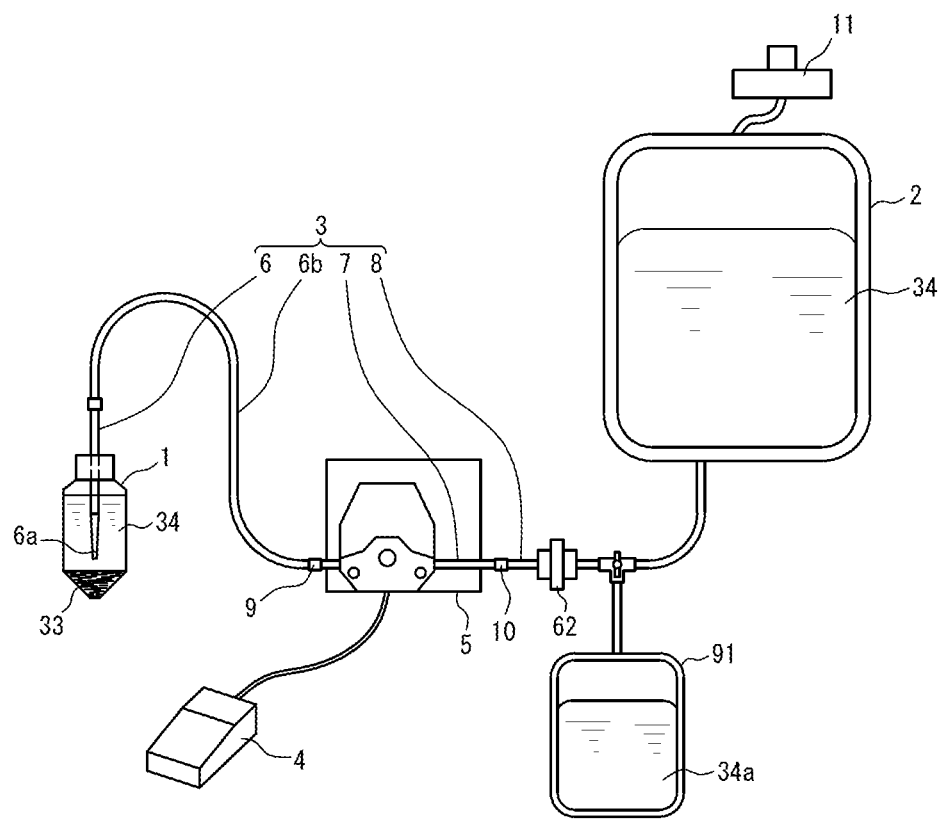
FIG. 13A is a schematic view showing an example where the sterility test membrane filter and a three-way stopcock are placed continuously according to the present invention.

The example shown in FIG. 13A is a configuration in which the sterility test membrane filter 62 and the three-way stopcock 81 are placed continuously, and the remaining port of the three-way stopcock 81 is connected to another container 91 having the culture medium 34 inside thereof. Therefore, in the example shown in FIG. 13, the fluid that has passed through the sterility test membrane filter 62 can be delivered to the container 91 that is different from the container 2 through an operation of the three-way stopcock 81.

Figure 13B:
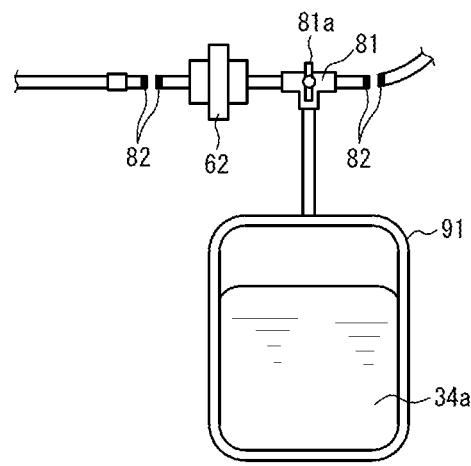
FIG. 13B is a schematic view showing a separated state where before and after the sterility test membrane filter and the three-way stopcock are sealed by a heat seal.

Further, when the example shown in FIG. 13A is configured as in FIG. 13B to be able to apply the culture medium 34a from the remaining port of the three-way stopcock 81 by sealing both the left and right sides of the drainage tube 8 sandwiching the sterility test membrane filter 62 and the three-way stopcock 81 by a heat seal 82 and the culture medium is filled inside the container 91 to be connected, it is possible to conduct an operation of the sterility test while preventing splashing of the solution to the outside.

In a case where a foreign matter is contained in the fluid to be delivered by the fluid delivery system, physical failures or chemical failures may be generated in the delivery channel 3 due to the foreign matter contained in the fluid.

Figure 14:
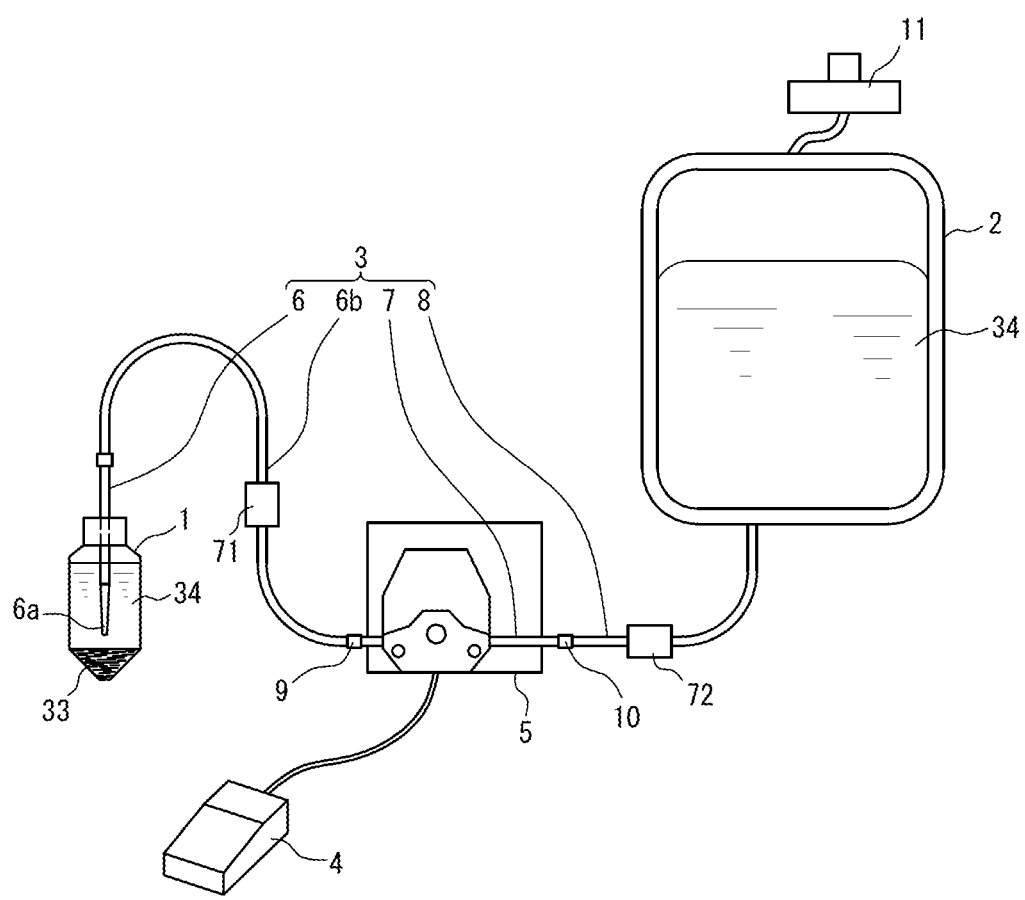
FIG. 14 is a schematic view showing an example where a foreign-matter removal filter is placed to the drainage tube according to the present invention.

An example shown in FIG. 14 can prevent mixture of the foreign matter into the other container through connecting foreign-matter removal filters 71, 72 for adsorbing the foreign matter in the middle of the aspiration tube 6b and the drainage tube 8 and delivering the fluid to the container 2 via the foreign-matter removal filters 71, 72. While FIG. 14 shows the example where the two foreign-matter removal filters are placed, it is also possible to employ a mode where either one of the filters is placed.

INDUSTRIAL APPLICABILITY

The present invention can deliver a fluid aseptically, and can be utilized when transferring a waste fluid after culturing cells used for immuno-cell therapy and regenerative medicine, for example. Furthermore, the present invention can also be utilized when transferring a culture solution to another container in a process of scaling up a culture system, and its applicable range is broad.

The invention claimed is:

1. A fluid delivery system for delivering a fluid from one container to another container, the fluid delivery system comprising:
    a delivery channel connecting between the one container to the other container, the fluid being transferred inside of the delivery channel; and
    a delivery pump that is configured with:
        a rotation member that rotates around a shaft;
        a plurality of rollers that are provided at an outer peripheral edge of the rotation member; and
        a support member that faces the rotation member and at least one of the plurality of rollers so as to sandwich the delivery channel with the one of the plurality of rollers, the support member being configured with first, second, and third planar surfaces that are continuously connected to each other so that the second planar surface is located between the first and third planar surfaces,
    wherein the fluid is transferred via the delivery channel by compressively deforming an inner diameter of the delivery channel by the plurality of rollers,
    wherein the delivery channel is partially elastic, and the delivery channel forms a closed-system with the fluid flowing inside thereof between the one container and the another container and is isolated from outside,
    when the one of the plurality of rollers is adjacent to the first planar surface, a first gap exists between the one of the plurality of rollers and the first planar surface,
    when the one of the plurality of rollers is adjacent to the second planar surface, a second gap exists between the one of the plurality of rollers and the second planar surface, and
    the first gap is smaller than the second gap.

2. The fluid delivery system according to claim 1, wherein the delivery pump is configured to adjust a transfer speed of the fluid according to a fluid amount inside the one container in a process of transferring the fluid from the one container to the other container.

3. The fluid delivery system according to claim 2, wherein the delivery pump comprises a footswitch for linearly controlling the transfer speed of the fluid.

4. The fluid delivery system according to claim 1, wherein the other container comprises an air vent filter for suppressing an increase in an internal pressure thereof.

5. The fluid delivery system according to claim 4, wherein the air vent filter blocks circulation of the fluid by making contact with the fluid inside the other container.

6. The fluid delivery system according to claim 1, wherein the delivery channel comprises a pipet detachably on the one container side.

7. The fluid delivery system according to claim 1, wherein the delivery channel and the other container are integrated in a connected state.

8. The fluid delivery system according to claim 1, further comprising a filter configured to adsorb fungi and bacteria in the delivery channel of the closed-system.

9. The fluid delivery system according to claim 1, comprising a filter configured to eliminate a foreign matter in the delivery channel of the closed-system.

10. The fluid delivery system according to claim 1,
wherein the plurality of rollers are configured by first, second, and third rollers that are circumferentially spaced apart from each other by 120 degrees,
the first planar surface has first and second ends, the third planar surface has third and fourth ends, and the first end and the fourth end are located at outermost positions of the support member, and
when the first roller is located directly adjacent to the first end, the second roller is located directly adjacent to the fourth end.

* * * * *